United States Patent [19]

Yamaguchi et al.

[11] Patent Number: 4,798,664
[45] Date of Patent: Jan. 17, 1989

[54] ION SENSOR

[75] Inventors: Shuichiro Yamaguchi, Fuji; Norihiko Ushizawa, Fujinomiya; Takeshi Shimomura, Fujinomiya, all of Japan

[73] Assignee: Terumo Kabushiki Kaisha, Tokyo, Japan

[21] Appl. No.: 946,089

[22] Filed: Dec. 24, 1986

[30] Foreign Application Priority Data

Dec. 25, 1985 [JP] Japan ................ 60-290812
Dec. 28, 1985 [JP] Japan ................ 60-299000
Jan. 21, 1986 [JP] Japan ................ 61-10737

[51] Int. Cl.⁴ .................................... G01N 27/30
[52] U.S. Cl. ............................ 204/418; 204/408; 204/416
[58] Field of Search ............ 204/416, 418, 419, 408; 128/635

[56] References Cited

U.S. PATENT DOCUMENTS

| | | | |
|---|---|---|---|
| 3,598,713 | 8/1971 | Baum et al. | 204/1 T X |
| 3,926,764 | 12/1975 | Ruzicka et al. | 204/195 |
| 3,932,233 | 1/1976 | Ruzicka et al. | 204/418 |
| 3,957,612 | 5/1976 | Niedrach et al. | 204/195 |
| 3,957,613 | 5/1976 | Macur | 204/195 |
| 4,115,209 | 9/1978 | Fraiser et al. | 204/1 T |
| 4,214,968 | 7/1980 | Battaglia et al. | 204/195 |
| 4,280,889 | 7/1981 | Szonntagh | 204/408 |
| 4,282,079 | 8/1981 | Chang et al. | 204/420 |
| 4,305,802 | 12/1981 | Koshiishi | 357/25 X |
| 4,512,870 | 4/1985 | Kohara et al. | 204/416 |
| 4,549,951 | 10/1985 | Knudson et al. | 204/416 |
| 4,561,962 | 12/1985 | Kankare | 204/415 |
| 4,563,263 | 1/1986 | Oyama et al. | 204/418 |
| 4,615,954 | 10/1986 | Solomon et al. | 429/27 |
| 4,632,732 | 12/1986 | Fog et al. | 204/1 T |

FOREIGN PATENT DOCUMENTS

| | | | |
|---|---|---|---|
| 56283 | 7/1982 | European Pat. Off. | |
| 01186210 | 7/1986 | European Pat. Off. | 204/418 |
| 3134760A | 9/1982 | Fed. Rep. of Germany | 204/416 |
| 52-30490 | 8/1977 | Japan | 204/431 |
| 57-6344 | 4/1982 | Japan | 204/418 |
| 57-196116 | 12/1982 | Japan | 204/416 |
| 83167951 | 10/1983 | Japan | |
| 59-57156 | 4/1984 | Japan | 204/416 |
| 59-164952 | 9/1984 | Japan | 204/416 |
| 60-7357 | 1/1985 | Japan | 204/416 |
| 60-52759 | 3/1985 | Japan | 204/416 |
| 60-73351 | 4/1985 | Japan | 204/416 |
| 898314 | 1/1982 | U.S.S.R. | |

OTHER PUBLICATIONS

Oyama et al., "Ion Selective Electrode Prepared by Modifying an Electrode with Polymers", *Tokyo Seminar on Macromolecular Complexes*, Tokyo Univ., Oct. 14-17, 1987.
Ma et al., "Organic Analysis Using Ion-Selective Electrodes," Academic Press, 1982, pp. 62 and 70.
Ryan, "Electrochemical Detectors Fundamental Aspects and Analytical Applications," Plenum Press, 1985, p. 7.
Ammann, "Ion-Selective Microelectrodes", Principles, Design & Application, pp. 5-7, 66 & 100.
Oyrama et al. "Electrochemical Properties of Electropolymerized Poly (1-Pyrenamine) Films", The Chemical Society of Japan, Jul. 1986.
Ma et al., "Organic Analysis Using Ion-Sensitive Electrodes", vol. 2, pp. 60 & 62.

(List continued on next page.)

*Primary Examiner*—G. L. Kaplan
*Attorney, Agent, or Firm*—Burns, Doane, Swecker & Mathis

[57] ABSTRACT

Disclosed is a solid-type ion sensor which does not have an internal liquid chamber. The ion sensor has a laminated structure basically includes an electrically conductive substrate, a redox layer having a redox function covering the surface of the electrically conductive substrate, and an ion-selective layer covering the surface of the redox layer. Also provided is an ion sensor of this type having an insulated thermister imbedded so as to contact the redox layer.

47 Claims, 7 Drawing Sheets

OTHER PUBLICATIONS

*Bioelectroanalytical Chemistry Symposium*, Honolulu, Hi., Oct. 18-23, 1987.

Tamura et al., "Coated Wire Sodium-and Potassium-Electrodes Based on Bis(Crown Ether) Compounds", *Analytical Chemistry*, vol. 54, No. 7, Jun. 1982, pp. 1224-1227.

Wuthier et al., "Tin Organic Compounds as Nuetral Carriers for Anion Selective Electrodes", *Analytical Chemistry*, vol. 56, No. 3, Mar. 1984, pp. 535-538.

Norov et al., "Calcium-Selective Electrode Without an Internal Reference Solution", *Journal of Analytical Chemistry*, vol. 34, No. 8, Part 1, Aug. 1979, pp. 1159-1162.

Oyama et al., "Hydrogen Ion Selective Microelectrode Prepared by Modifying an Electrode with Polymers", *Analytical Chemistry 1987, vol. 59, pp. 258-262.*

Oyama, "Ion Selective Microelectrode Prepared by Modifying an Electrode with Polymers", *International Electrical Symposium*, Schaumberg, Ill., May 27-29 (1987), pp. 122-125.

Oyama et al., "A New Type of Ion-Selective Microelectrodes Using Electropolymerize Thin Films", j-4

- TEMPERATURE LOWERED
○ TEMPERATURE RAISED

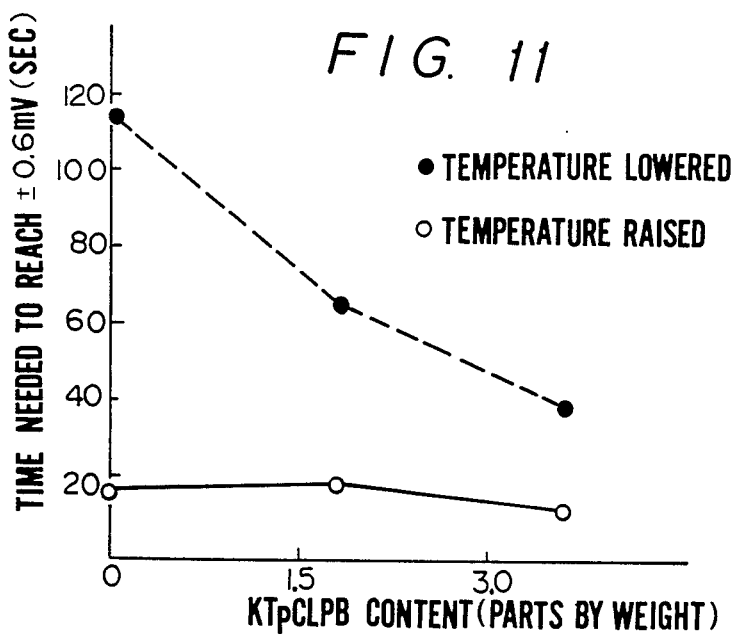
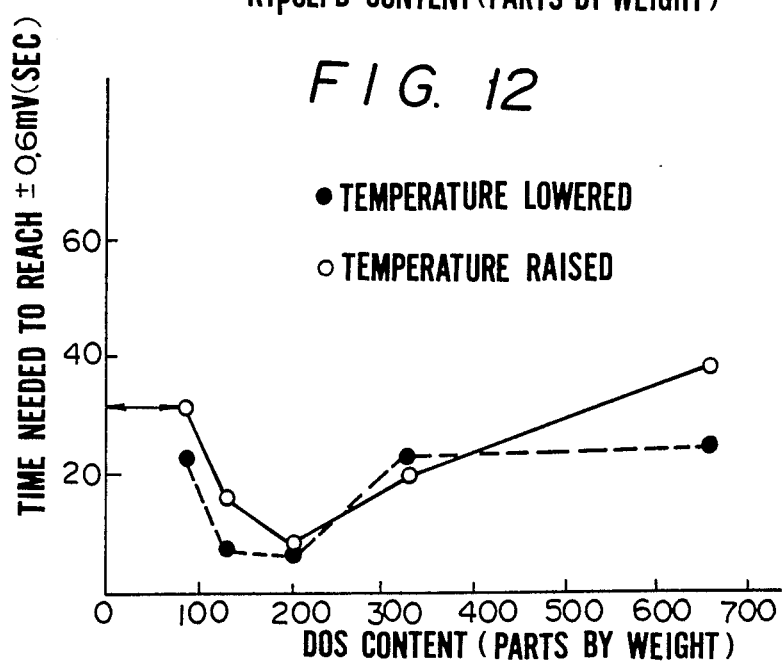

ION SENSOR

BACKGROUND OF THE INVENTION

1. Field of the Invention

This invention relates to an ion sensor and, more particularly, to an ion sensor exhibiting a high speed of response, an excellent temperature response and stable operation.

2. Description of the Prior Art

An ion sensor most commonly used in the prior art is constituted by a glass membrane electrode. However, the glass membrane in such an electrode breaks easily, and frequent washing is necessary since measurements taken thereby are influenced by the existence of interfering ions, medicines, the proteins in a living body, amino acids and trace amounts of active ingredients. These and other inconveniences are encountered in terms of use.

PH electrodes using a polymeric membrane have recently been reported as an improvement on the glass membrane electrode. For example, a liquid membrane electrode is described in *Analytical Chimica Acta*, 131, (1981), pp. 111-116, and a solid membrane electrode is disclosed in Japanese Patent Application No. 59-281076. However, since these electrodes possess an internal liquid chamber just as the glass membrane electrode, they do not fundamentally solve the problems of the glass electrode and are not fully satisfactory.

These conventionally employed ion sensors generally can be used for measurements at a constant temperature. A change, especially a rapid one, in the temperature of a liquid specimen has a profound effect upon the sensor characteristics (speed of response, transient response, etc.). It is common technical knowledge that measurement of ionic concentration using an electrode having an internal liquid chamber is performed under constant temperature conditions.

However, ionic concentration measurements for clinical examinations and the like are now being performed under increasingly harsh conditions. In addition to the ability to perform measurements precisely, these sensors must have characteristics that (1) enable ionic concentration measurements to be performed continuously and (2) enable ionic concentration measurements to be performed accurately even if there is a sudden change in the temperature of a liquid specimen.

Since the conventional glass membrane electrode requires washing within 30 minutes at most for the reasons set forth above, it is difficult to use the electrode for continuous ionic concentration measurement in a closed system. Though the polymeric membrane electrode, as an alternative to the glass membrane electrode, has been studied to some degree, with relation to the temperature characteristics of the electrode at equilibrium temperature, transient phenomenon accompanying temperature changes have hardly been investigated. This is because it is difficult to measure temperature distribution due to the structure of such an electrode.

Membrane-coated solid electrodes can be made very small. They also do not have an internal liquid chamber and, hence, there is no risk of an internal liquid leaking and contaminating a specimen undergoing measurement. For these reasons, electrodes of this type are attracting considerable interest since they are well-suited for use as clinical sensors.

One requirement that must be satisfied before a membrane-coated solid electrode can be used practically is a high speed of response. In general, response speed tends to vary in inverse proportion to membrane thickness. With a large membrane thickness, an ion carrier membrane-coated solid electrode, in which an ion carrier substance is contained in a polyvinyl chloride (PVC) polymer, exhibits an electrode membrane resistance having a high value of 100 M$\Omega$ or more. If a thin ion carrier membrane is adopted, however, sensor characteristics deteriorate in a short period of time, rendering the electrode unsuitable for practical use. Accordingly, the ideal membrane thickness is on the order of 0.8-1.2 mm, in which case the membrane resistance will be 70-100 M$\Omega$. Since membrane resistance approximately doubles when the temperature drops by 10° C., problems are encountered when taking measurements at low temperatures. The inventor has found that when the electrode membrane resistance exceeds 50 M$\Omega$, the amount of noise increases and it is difficult to measure the electromotive force of the ion sensor accurately.

Though one method of reducing membrane resistance is to enlarge the electrode area, a greater electrode area necessarily results in a larger electrode. However, an ion small sensor is essential when considering such clinical examination requirements as (1) the ability to measure trace amounts of a liquid specimen, (2) a sensitive reaction to changes in temperature, and (3) the ability to directly measure ionic concentration in body fluids using a catheter or the like. A small sensor has an electrode with a low thermal capacity and attains temperature equilibrium quickly even if there is a sudden change in the temperature of the liquid specimen. Such a sensor is considered to be highly sensitive to temperature changes.

SUMMARY OF THE INVENTION

The inventor has performed exhaustive research in an effort to reduce the size of an ion sensor comprising a membrane-coated solid electrode in which the electrode membrane resistance of the ion carrier membrane is less than 50 M$\Omega$ even at a temperature of 10° C. As a result of this research, the inventor has found that this objective is attained if a stick-shaped member is used as an electrically conductive substrate and the membrane is deposited on the tip surface and the tip side of the member. The invention has been perfected on the basis of this discovery.

More specifically, the present invention provides an ion sensor characterized in that an ion carrier membrane is deposited on the surface of a stick-shaped electrically conductive substrate obtained by depositing a membrane having a redox function on the outer circumferential surface or on the outer circumferential surface and tip surface of the substrate.

In a preferred embodiment, the ion carrier membrane used in the present invention has an electrode membrane resistance of less than 50 M$\Omega$ at 10° C.

The electrically conductive substrate used in the ion sensor of the invention may consist of an electrically conductive carbon material such as basal-plane pyrolytic graphite (hereafter referred to as "BPG") or glassy carbon, a metal such as gold, platinum, copper, silver, palladium, nickel or iron, especially a precious metal, or a composite obtained by coating the surface of any of these metals with a semiconductor such as indium oxide or tin oxide. The electrically conductive carbon material is preferred, especially BPG. In order to make the conductive substrate small in size, a stick-shaped member is used and a membrane having a redox function is deposited over an area of 1–20 mm² on the outer circumferential surface of the stick-shaped substrate or on its outer circumferential surface and tip surface. A lesser area is undesirable as it will cause electrode membrane resistance of the ion carrier membrane to exceed 50 MΩ at 10° C.; a larger area will result in an ion sensor which is no longer small in size. Though the stick-shaped substrate may be of a cylindrical, prismatic or like configuration, the cylindrical substrate having a rounded tip is especially preferred in terms of moldability and membrane adhesion. Conventionally, the basal plane of BPG is utilized as the electrode plane. However, the inventor has discovered that the edge plane of BPG can also be effectively exploited, and that because of this, a stick-shaped electrode can be fabricated even from BPG. BPG is highly preferred since it excels in terms of sensor operating stability. A stick of BPG, for example, cylindrial shaped, will exhibit excellent strength especially if the diameter selected is 0.1–2 mm.

The redox layer refers to one, in which an electrode comprising an electrically conductive substrate having this layer deposited on its surface, capable of generating a constant potential on the substrate owing to a redox reaction. In the present invention, an especially preferred redox layer is one which will not allow the potential to fluctuate due to the partial pressure of oxygen gas. Particularly suitable examples of the redox layer are (1) an organic compound membrane or a polymeric membrane capable of a quinone-hydroquinone type redox reaction, (2) an organic compound membrane or polymeric membrane capable of an amine-quinoid type redox reaction, and (3) poly (pyrrole) and poly (thionylene) compound type electro conductive substrates. The quinone-hydroquinone type redox reaction is expressed, by e.g., the following reaction formula, taking a polymer as an example:

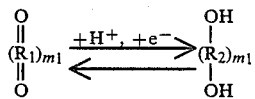

where $R_1$, $R_2$, represent e.g., compounds having a structure containing an aromatic series.

The amine-quinoid type redox reaction is expressed by, e.g., the following reaction formula, taking a polymer as an example:

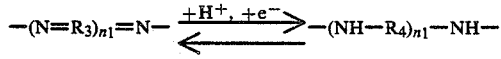

$R_3$, $R_4$, represent e.g., compounds having a structure containing an aromatic series.

The following compounds (a)–(d) can be mentioned as compounds capable of forming the abovementioned layer having the redox function:

(a) A hydroxy aromatic compound expressed by

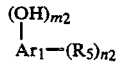

where $Ar_1$ represents an aromatic nucleus, $R_5$ a substituent group, $m_2$ is 1 to the effective valence of $Ar_1$, and $n_2$ is 0 to the effective valence of $Ar_1$ minus 1.

The aromatic nucleus of $Ar_1$ may be a single ring such as a benzene nucleus, a multiple ring such as an anthracene nucleus, pyrene nucleus, chrysene nucleus, perylene nucleus or coronene nucleus, or a heterocyclic ring. Examples of the substituent group $R_5$ are alkyl groups such as a methyl group, aryl groups such as a phenyl group, and a halogen atom. More specifically, examples are dimethyl phenol, phenol, hydroxy pyridine, o- and m-benzyl alcohols, o-, m- and p-hydroxybenzaldehydes, o- and m-hydroxyacetophenones, o-, m- and p-hydroxypro-piophenons, o-, m- and p-hydroxybenzophenones, o-, m- and p-carboxyphenols, diphenylphenol, 2-methyl-8-hydroxy-quinoline, 5-hydroxy-1, 4-naphthoquinone, 4-(p-hydroxy-phenyl)2-buthanone, 1, 5-dihydroxy-1, 2, 3, 4-tetra-hydronaphthalene, bisphenol-A, salicylanilide, 5- and 8-hydroquinolines, 1,8-dihydroxyanthraquinone, and 5-hydroxy-1,4-naphthoquinone.

(b) An amino aromatic compound expressed by the formula

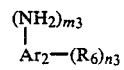

where $Ar_2$ represents an aromatic nucleus, $R_6$ a substituent group, $m_3$ is 1 to the effective valence of $Ar_2$, and $n_3$ is 0 to the effective valence of $Ar_2$ minus 1.

As for the aromatic nucleus $Ar_2$ and the substitution group $R_6$, items similar to $Ar_1$ and the substitution group $R_5$ in compound (a) can be used. Specific examples of the amino aromatic compound are aniline, 1,2-diaminobenzene, aminopyrene, diaminopyrene, aminochrysene, diaminochrysene, 1-aminonaphtalene, 9-aminonaphthalene, 9, 10-diaminonaphthalene, 1-aminoanthraquinone, p-phenoxyaniline, o-phenylenediamine, p-chloroaniline, 3,5-dichloroaniline, 2,4,6-trichloroaniline, N-methylaniline, and N-phenyl-p-phenylenediamine and so on.

(c) A quinone such as 1,6-pyrenequinone, 1,2,5,8-tetrahydroxynalizaline, phenanthrenequinone, 1-aminoanthraquinone, purpurine, 1-amino-4-hydroxyanthraquinone, and anthralphyne.

Among these compounds, 2,6-xylenol and 1-aminopyrene are especially preferred.

(d) Pyrrole and derivatives thereof (e.g. N-methyl pyrrole), and thiophene and derivatives thereof (e.g. methyl thiophene).

Further, examples of compounds capable of forming the layer having the redox function are those which undergo a redox reaction. The following can be mentioned: poly(N-methyl aniline) [Onuki, Matsuda, Oyama, Nihon Kagakukaishi, 1801–1809 (1984)], poly(2,6-dimethyl-1,4-phenylene ether), poly(o-phenylediamine), poly(phenol) and polyxylenol; organic compounds containing the compounds (a) through (d) such as pyrazoroquinone group-containing vinyl compound-polymers, isoaroxythazine group-containing vinyl compound-polymers and other quinone group-containing compound-polymers, lower polymeric compounds (oligomers) of compounds (a) through (d), or substances obtained by fixing the compounds of (a) through (d) to polymeric compounds such as polyvinyl compounds and polyamide compounds. In the present specification, the term "polymer" is taken to mean both homopolymers and mutual polymers such as copolymers.

In the present invention, in order to deposit the compound capable of forming the redox layer on the an electrically conductive substrate, a polymer is dissolved in a solvent. This polymer is obtained by: (1) synthesizing an amino aromatic compound, a hydroxy aromatic compound, or the like, on an electrically conductive substrate, of electrically conductive carbon or a precious metal, by an electrolytic oxidation polymerization method or electrodeposition method; or (2) synthesized by application of electron beam irradiation, light or heat. The resulting solution is (a) deposited on the electrically conductive substrate by painting or dipping, (b) reacted in the gas phase in vacuo and deposited directly on the electrically conductive substrate, or (c) irradiated with light, heat or radiation for deposit directly on the electrically conductive substrate. Among these three methods, the most preferred is the, electrooxidation polymerization method. The electrolytic oxidation polymerization method is implemented by subjecting the amino aromatic compound or hydroxy aromatic compound to electrolytic oxidation polymerization in a solvent in the presence of a suitable supporting electrolyte and depositing a layer of the polymer on the surface of the electrically conductive substrate. Preferred examples of the solvent are acetonitrile, water, dimethyl formamide, dimethyl sulfoxide, propylene carbonate, methanol and the like. Preferred examples of the supporting electrolyte are sodium perchlorate, sulfuric acid, sodium sulfate, phosphoric acid, boracic acid, tetraofluoro-potassium phosphate, quaternary ammonium salts and the like.

The membrane thickness of the redox layer is 0.01 μm–1.0 mm, preferably 0.1 μm–0.1 mm. A membrane thickness of less than 0.01 μm does not fully bring forth the effects of the invention, while a thickness of more than 1.0 mm is undesirable from the viewpoint of miniaturizing the sensor.

The redox layer used in the present invention can be used in a form impregnated with an electrolyte. Examples of the electrolyte are phosphoric acid, dipotassium hydrogen phosphate, sodium perchlorate, sulfuric acid, tetrafluoro borate, tetraphenyl borate and the like. In order to impregnate the redox layer with the electrolyte, a simple method, which can be adopted, is to coat the electrically conductive substrate with the redox layer and then dip the resulting membrane into a solution of the electrolyte.

As the ion-sensitive layer, which is coated on the surface of the redox layer, use can be made of a membrane (a neutral carrier membrane) containing an ion carrier material selective to the ion of interest and, if necessary, an electrolytic salt, are carried on a polymeric compound. The following are examples of the ion carrier material which can be used, depending upon the ion of interest:

(i) For hydrogen ion

Examples of a hydrogen ion carrier material are amines expressed by the formula

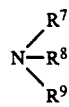

(where $R^7$, $R^8$, $R^9$ represent the same or different alkyl groups, among which at least two alkyl groups have a carbon number of 8–18), and compounds expressed by the formula

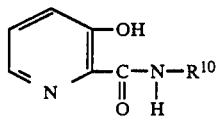

(where $R^{10}$ represents an alkyl group having a carbon number of 8–18). Tri-n-dodecylamine is especially preferred.

(ii) For potassium ion

Examples of which can be mentioned are valinomycin, nonactin, monactin, crown ether compounds such as dicyclohexyl-18-crown-6, naphtho-15-crown-5, bis(15-crown-5) and the like. Among these, valinomycin and bis(15-crown-5) are ideal.

(iii) For sodium ion

Examples which can be mentioned are aromatic amides or diamides, aliphatic amides or diamides, and crown compounds, e.g. bis[(12-crown-4)methyl]-dodecylmalonate, N,N,N,N-tetrapropyl-3,6-dioxanate diamide, N,N,N',N'-tetrabenzyl-1,2-ethenedioxy diacetoamide, N,N'-dibenzyl-N,N'-diphenyl-1,2-phenylenediacetoamide, N,N',N''-triheptyl-N,N'N''-trimethyl-4,4',4''-propyridine tris(3-oxythabutylamide), 3-methyoxy-N,N,N,N-tetrapropyl-1,2-phenylene dioxydiacetoamide, (-)-(R,R)-4,5-dimethyl-N,N,N,N-tetrapropyl-3,6-dioxaoctanediamide, 4-methyl-N,N,N,N-tetrapropyl-3,6-dioxaoctane diamide, N,N,N,N-tetrapropyl-1,2-phenylenedioxydiacetoamide, N,N,N,N-tetrapropyl-2,3-naphthanedioxydiacetoamide, 4-t-butyl-N,N,N,N-tetrapropyl-1,2-dicyclohexanedioxydiacetoamide, cis-N,N,N,N-tetrapropyl-1,2-cyclohexanedioxydiacetoamide, and trans-N,N,N,N-tetrapropyl-1,2-cyclohexanedioxydiacetoamide. Among these, bis[(12-crown-4) methyl] dodecylmalonate is well-suited for use.

(iv) For chlorine ion

Examples which can be mentioned are quaternary ammonium salts expressed by the formula

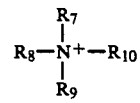

(where Rhu 7, $R^8$, $R^9$ represent the same or different alkyl groups having a carbon number of 8–18, and $R_{10}$ represents hydrogen or an alkyl group having a carbon number of 1–8, and a triphenyl tin chloride expressed by the formula

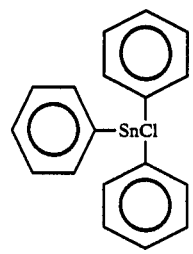

(v) For calcium ion

Suitable examples are bis[di-(n-octylphenyl) phosphate], (-)-(R,R)-N,N'-bis[(11-ethoxy carbonyl) undecyl]-N,N',4,5-tetramethyl-3,6-dioxaoctanediamide and calcium bis[di(n-decyl) phosphate].

(vi) For hydrogencarbonate ion

Examples which can be mentioned are a quaternary ammonium salts expressed by the formula

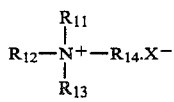

(where $R_{11}$, $R_{12}$, $R_{13}$ represent the same or different alkyl groups having a carbon number of 8-18, $R_{14}$ represents hydrogen atom or an alkyl group having a carbon number of 1-4, and $X^-$ represents $Cl^-$, $Br^-$ or $OH^-$), tertiary amine compounds expressed by the formula

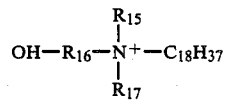

(where $R_{15}$ represents a phenyl group, hydrogen atom or a methyl group, $R_{16}$ represents hydrogen atom or a methyl group, and $R_{17}$ represents a methyl group or an octadecyl group), and a compound expressed by the formula

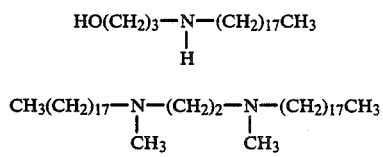

Examples of the electrolytic salt are sodium tetrakis(p-chlorophenyl) borate, potassium tetrakis(p-chlorophenyl) borate, and a compound expressed by the formula

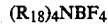

$(R_{18})_4NBF_4$ where $R_{18}$ represents an alkyl group, preferably an alkyl group having a carbon number of 2-6.

(vii) For ammonium ion

Suitable example are nonachtine + monachtine, tetranachtine, etc.

Examples of the polymer compound are organic polymer compounds such as vinyl chloride resin, vinyl chloride-ethylene copolymer, polyester, polyacryl amide and polyurethane, and inorganic polymer compounds such as silicone resin. Compounds are used in which the plasticizer does not readily elute. Examples of such a plasticizer are dioctyl sebacate ester, dioctyl adipate ester, dioctyl maleate ester and di-n-octyl phenylphosphonate, o-nitrophenyl octyl ether.

In order to coat the surface of the redox layer on the electrically conductive substrate with the ion-sensitive layer, having the foregoing composition, 50-50 parts by weight of the plasticizer, 0.1-50 parts by weight of the ion carrier material (both with respect to 100 parts by weight of the polymer compound serving as the carrier) and the electrolytic salt are dissolved in a solvent (e.g. tetrahydrofuran). The resulting solution is placed on the electrically conductive substrate to a thickness of 0.1 μm - 10 mm and then dried at room temperature or under heating. Alternatively, the electrically conductive substrate is dipped into the solution followed by drying in a similar manner. It is desired that the thickness of the applied ion-sensitive layer be 1 μm - 10 mm.

By virtue of the above construction, the ion sensor has a comparatively large electrode surface area despite its extremely small size, and the electrode membrane resistance can be made less than 50 MΩ at the necessary 10° C., thus making measurements at low temperature feasible.

For an ion sensor, small size is not only necessary for clinical examinations but is also very important in terms of general-purpose applications. In addition, small size means a sensitive response to variations in the temperature of a liquid specimen.

Besides exhibiting the aforementioned advantages, the inventive sensor having a deposited membrane, which does not readily dissolve in a plasticizer, obtained by electrolytic oxidation polymerization at a specific temperature, operates stably even when used at high temperatures. The sensor therefore is usable over a wide temperature range of from 10° to 45° C. This has important practical advantages.

In order to satisfy modern day demands, the inventor considered it important for an ion sensor to have an electrode devoid of an internal liquid chamber and to be capable of continuous monitoring temperature whenever necessary. As the result of exhaustive research in this area, the inventor discovered that if a solid-type ion sensor is adopted in which a membrane having a redox function is deposited on the surface of an electrically conductive substrate, it is possible to mount a temperature sensor without use of an internal liquid chamber. The invention has been perfected on the basis of this discovery.

More specifically, in another aspect thereof, the present invention provides an ion sensor characterized in that a membrane having a redox function is deposited on the surface of an electrically conductive substrate, an ion carrier membrane is then deposited on the surface of redox membrane to form an ion sensor, and a thermister coated with an insulating film is imbedded in the ion carrier membrane so as to contact the redox membrane.

The thermister is one which can be incorporated in a miniature electrode. Preferably, the smaller the thermister the better, with one having an outer diameter of no more than 1 mm being ideal. Though the higher the speed of response the better, ordinarily a thermister having a time constant of one second or less can be used. In order to prevent dissipation of heat through the lead wires of the thermister, it is preferred that the lead wires consist of a material exiibiting poor thermal conduction and that they be as fine as possible without causing durability problems. The thermister used is coated with an insulating film, preferably one which is chemically inert. An example which can be mentioned is a Teflon tube. Ideally, the film should be thin from the standpoint of the thermal conductivity.

Monitoring the internal temperature by means of the thermister imbedded in the inventive ion sensor can be performed in accordance with any ordinary method.

The ion sensor of the invention does not possess an internal liquid chamber and has a membrane which exhibits excellent selectivity. This makes it possible to use the sensor continuously over an extended period of time. Since the sensor has internal thermister, as mentioned above, a temperature difference between a liquid specimen and the interior of the electrode can be monitored. For example, this makes it possible to determine whether a transient response, accompanying a change in temperature of the liquid specimen, is due to an unsteady temperature or a delay in the sensor response. This enables a more accurate measurement of ion concentration without the influence of temperature changes.

The inventor has performed exhaustive research in an effort to provide an ion sensor having an improved response with respect to a step-like change in temperature. As a result of this research, the inventor has found that the abovementioned solid membrane-type sensor exhibits a significantly different step response depending upon the composition of the ion carrier membrane. The invention has been perfected on the basis of this discovery.

Specifically, in a preferred embodiment, the present invention provides an ion sensor for measuring the ionic concentration of a solution on the basis of electrode potential response. The ion sensor includes a film having a redox function provided on the surface of an electrically conductive substrate, and an ion carrier membrane provided on the surface of the redox film, the ion carrier membrane containing the following ingredients (A) - (D):

| | |
|---|---|
| (A) unplasticized polyvinyl chloride: | 100 parts by weight |
| (B) ion carrier material: | 6–30 parts by weight |
| (C) electrolyte | 0–3.6 parts by weight |
| (D) plasticizer | 40–665 parts by weight |

If the load of the ion carrier material is less than 6 parts by weight with respect to 100 parts by weight of the unplasticized polyvinyl chloride, a satisfactory temperature response is not obtained. An ion carrier load of more than 30 parts by weight with respect to 100 parts by weight of the unplasticized polyvinyl chloride is unsuitable because the ion carrier membrane will harden as a result. The preferred range is 9 to 24 parts by weight.

The load of the electrolyte preferably is equal to or less than that of the ion carrier material. Too small a load will increase the membrane resistance and worsen the temperature response. It is preferred that the electrolyte load be 0 to 3.6 parts by weight with respect to 100 parts by weight of the unplasticized polyvinyl chloride.

The polyvinyl chloride (PVC) functions as a carrier for the ion carrier material and electrolyte and should maintain a fixed shape after the membrane is formed. The PVC preferably has an average polymerization ($p_n$) of 500–2500.

If the loading ratio of the plasticizer is too low with respect to 100 parts by weight of the unplasticized polyvinyl chloride in the ion carrier membrane, the electrode obtained will not be capable of functioning as a sensor. If the loading ratio of the plasticizer is too high, the unfortunate result will be a slower temperature step response. Thus, the desired ratio is 40–665 parts by weight, with 80–330 parts by weight being especially preferred.

By virtue of the above construction, the ion sensor of the invention is capable of attaining an equilibrium value within ten seconds with regard to a sudden temperature change of 20° C. or more. This makes possible accurate measurement of ionic concentration even in a flow system where the temperature of the liquid specimen undergoes a rapid change.

It goes without saying that the present invention is applicable not only to ion sensors but also to biosensors such as oxygen sensors, gas sensors and the like.

BRIEF DESCRIPTION OF THE DRAWINGS

FIGS. 8 and 9 illustrate response curves of the electromagnetic force of the inventive sensor with respect to step-like changes in the temperature of a liquid specimen, in which FIG. 8 shows the curve for a temperature rise and FIG. 9 shows the curve for a temperature drop; and FIGS. 10, 11 and 12 are graphs showing the relationship between the response of a PH sensor with respect to a step-like change in temperature and the composition of a hydrogen ion carrier membrane.

DETAILED DESCRIPTION

An embodiment will now be described in which the present invention is applied to a PH sensor serving as a typical example of an ion sensor.

EXAMPLE 1

Figure 1:
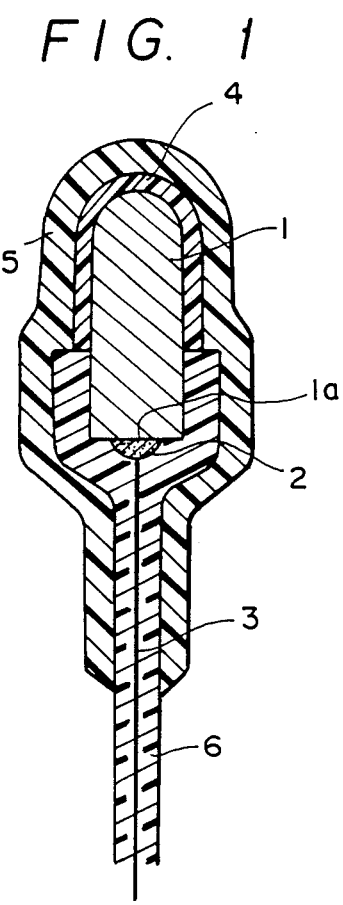
FIG. 1 is a sectional view showing an internal structure of a PH sensor according to the present invention.

A PH sensor shown in FIG. 1 was fabricated in accordance with the following steps:

(1) Fabrication of redox membrane electrode

A lead wire 3 made of copper and having a diameter of 0.2 mm$\phi$ was fixed by means of an electrically conductive adhesive 2 (C-850-6, manufactured by Amicon) to the circular bottom surface 1a of a cylinder (1.0 mm in diameter and 3.5 mm in length) of BPG 1, the bottom surface and outer circumferential surface of which are the basal plane and edge plane, respectively. The lead wire 3 and BPG 1 were insulated by being coated with a Teflon paint 6 (Polyflon TC-7408GY, manufactured by Daikin Kogyo).

Next, the paint 6 was cut away at the tip of the BPG 1 and at the contiguous circumferential surface, to expose a 1.6 mm length of the BPG. The tip portion was then cut into a hemispherical shape having an area of 4.87 mm$^2$. Electrolytic oxidation polymerization was performed uder the following conditions to directly coat the exposed surface of the BPG with an oxidative polymeric membrane 4, thereby fabricating a redox membrane electrode having a membrane thickness of 30 $\mu$m:

(Electrolyte Composition)

An acetonitrile solution consisting of 0.5 M 2,6-xylenol and 0.2 M NaClO$_4$ was employed as the electrolytic solution.

(Electrolytic Oxidation Conditions)

The BPG 1 was used as the working electrode, a saturated sodium chloride calomel electrode (SSCE) as a reference electrode, and a platinum mesh as counter electrode.

To perform electrolytic oxidation, the electrolytic polymerization temperature was held constant at −19.5° C. and the electrolyzing voltage was swept three times (sweep rate: 50 mV/sec) from 0 V (vs. the SSCE) to 1.5 V, followed by carrying out constant-potential electrolysis for 10 min at 1.5 V.

(2) Deposition of hydrogen ion carrier

A hydrogen ion carrier membrane 5 was deposited by repeatedly dipping the redox membrane electrode obtained in (1) above in a hydrogen ion carrier composition, given below, and allowing the same to dry. The dipping and drying steps were repeated 15 times to uniformly coat the surface of the redox membrane electrode with a hydrogen ion carrier membrane to a membrane thickness of about 1.0 mm.

| (Hydrogen Ion Carrier Composition) | |
| --- | --- |
| tridodecyl amine | 2 mg/ml |
| tetrakis(p-chlorophenyl) potassium borate | 1.2 mg/ml |
| polyvinyl chloride (PVC, p$_n$ = 1050) | 65.6 mg/ml |
| diocytl sebacate (DOS) | 131.2 mg/ml |
| solvent: tetrahydrofuran (THF) | |

EXAMPLES 2–4

PH sensors were fabricated as in Example 1 except for the fact the BPG substrates used were prismatic (0.8 mm×0.9 mm×2 mm) and plate-like (1.3 mm×0.3 mm×1.2 mm) in shape. In all cases the BPG substrates were such that the tip surface defined the edge plane.

EXPERIMENT 1

Electromotive force with regard to an SSCE was measured in a phosphoric acid buffer solution using the PH sensors fabricated in Examples 1–4, and electromotive force was plotted against PH. Hereafter, this will be referred to as a Nernst plot. The slope of each Nernst plot and the Na$^+$ ion selection coefficient $K_{H^+ Na^+}^{Pot}$ of each PH sensor were measured. For comparison purposes, a PH sensor in the shape of a circular disk (using solely the basal plane) was also investigated. The results are shown in Table 1.

TABLE

| BPG Substrate Shape | Area (mm$^2$) | Nernst Plot Slope (mV/PH) | -logk$_{H^+ Na^+}^{Pot}$ |
| --- | --- | --- | --- |
| Cylinder | 4.87 | −63.67 | 9.966 |
| Prism | 4.72 | −62.43 | 9.958 |
| Thin Plate | 4.55 | −65.00 | 9.935 |

TABLE -continued

| BPG Substrate Shape | Area (mm$^2$) | Nernst Plot Slope (mV/PH) | -logk$_{H^+ Na^+}^{Pot}$ |
| --- | --- | --- | --- |
| Circular Disk | 0.79 | −63.09 | 9.917 |

In Table 1, measurements were taken at a temperature of 37° C.

EXPERIMENT 2

(1) The membrane resistance of the PH sensor obtained in Example 1 was investigated at various temperatures. The results are shown in Table 2.

TABLE 2

| BPG Substrate Shape | Area (mm$^2$) | Membrane Resistance (MΩ) | | | | |
| --- | --- | --- | --- | --- | --- | --- |
| | | 5° C. | 15° C. | 25.2° C. | 37° C. | 44.5° C. |
| Cylinder | 4.87 | 15.7 | 7.52 | 4.06 | 2.01 | 1.39 |
| Circular Disk* | 0.79 | 156 | 123 | 60.6 | 31.7 | 20.8 |

Table 2 shows that membrane resistance approximately doubles with every 10° drop in temperature, exceeding 50 MΩ at low temperatures in case of the circular disk-shaped substrate.

(2) Using the PH sensors of the types mentioned above, electromotive force (vs. the SSCE) was measured in a standard solution as in Experiment 1. The measurements were taken over a standard solution temperature range of 10°–45° C. In order to reduce common mode noise, a differential-type electrometer was used to measure the electromotive force. The results show that while noise was within ±0.2 mV at all temperatures in case of the cylindrical substrate and, hence, did not impede measurement, noise was above ±0.5 mV at below 20° C. when the circular disk-shaped substrate was used, thus making it difficult to measure electromotive force accurately.

Referential Example

Redox membrane electrodes where fabricated as in Example 1(1) except for the fact that various electrolyzation polymerization temperatures were used. The solubility of the obtained membranes in DOS was investigated based on the absence or presence of the redox membrane and a change in the color of the DOS solution after the redox membrane was immersed in the DOS solution, the temperature whereof was 121° C., for eight hours. The results are shown in Table 3.

TABLE 3

| Polymerization Temperature (°C.) | Membrane Surface Color | Membrane Resistance (MΩ) | Solubility in DOS |
| --- | --- | --- | --- |
| 24.3 | Black | 59.6 | Partially solved |
| 0 | Black | 118.0 | Dissolved |
| −20.5 | Dark Green | 54.4 | Undissolved |
| −44.9 | Reddish Brown | 121.2 | Dissolved |

Table 3 shows that the membrane electrolyzation polymerized at −20.5° C. did not dissolve in DOS, and that the membrane was highly stable even at high temperatures. Accordingly, in order to obtain a PH sensor capable of operating stably for an extended period of time at high temperatures e.g. 45° C.), it is necessary to carry out electrolyzation polymerization at about −20° C.

By virtue of the above-described construction, the PH sensor of the present embodiment has a comparatively large electrode surface area despite the very small size of the sensor. The electrode membrane resistance of the hydrogen ion carrier membrane can be made less than 50 MΩ at the required temperature of 10° C., and measurements at low temperatures are possible.

For an ion sensor, small size is not only necessary for clinical examinations but is also very important in terms of general-purpose applications. In addition, small size means a sensitive response to variations in the temperature of a liquid specimen.

Besides exhibiting the aforementioned advantages, the inventive sensor having a deposited membrane, which does not readily dissolve in a plasticizer, obtained by electrolytic oxidation polymerization at a specific temperature operates stably even when used at high temperatures. The sensor therefore is usable over a wide temperature range of from 10° to 45° C. This has important practical advantages.

EXAMPLE 5

Figure 2:
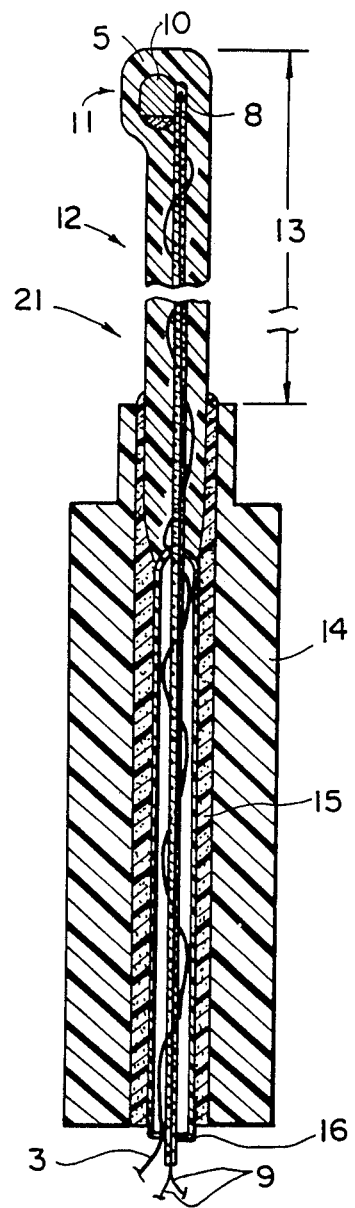
FIG. 2 is a sectional view showing internal structure of a PH sensor with thermister according to the present invention.
Figure 3:
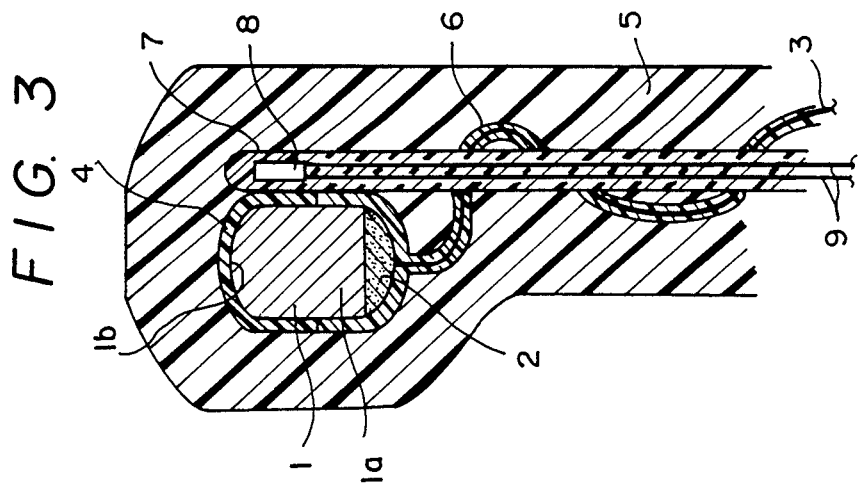
FIG. 3 is an enlarged sectional view useful in describing an electrode portion of the PH sensor shown in FIG. 2.

A PH sensor shown in FIGS. 2 and 3 was fabricated in accordance with the following steps:

(1) Fabrication of redox membrane electrode

The lead wire 3 made of copper and having a diameter of 0.2 mmφ was fixed by means of the electrically conductive adhesive 2 (C-850-6, manufactured by Amicon) to the circular bottom surface 1a of the cylinder (1.0 mm in diameter and 3.5 mm in length) of BPG 1. The lead wire 3 and BPG 1 were insulated by being coated with the Teflon paint 6 (Polyflon TC-7408GY, manufactured by Daikin Kogyo).

Next, the paint 6 was cut away at the tip 1b of the BPG 1 to expose a 1.8 mm length of the BPG. Electrolytic oxidation polymerization was performed under the following conditions to directly coat the exposed surface of the BPG with an oxidative polymeric membrane 4, thereby fabricating a redox membrane electrode 10 having a membrane thickness of 30 μm:

(Electrolyte Composition)

An acetonitrile solution consisting of 0.5M 2,6-xylenol and 0.2M $NaClO_4$ was employed as the electrolytic solution.

(Electrolytic Oxidation Conditions)

The BPG 1 was used as the working electrode, an Ag/AgCl electrode as a reference electrode, and a platinum mesh as a counter electrode.

To perform electrolytic oxidation, the electrolyzing voltage was swept three times (sweep rate: 50 mV/sec) from 0V (vs. the Ag/AgCl electrode) to 1.5V, followed by carrying out constant-potential electrolysis for 10 min at 1.5V.

(2) Mounting of thermister

As shown in FIGS. 2 and 3, a thermister 8 covered and insulated by a Teflon tube 7 was mounted in the vicinity of the redox membrane 4 of the redox membrane electrode 10, fabricated as set forth above, so as to contact the redox membrane 4 through the Teflon tube 7. The thermister 8 used had a resistance value of 2530Ω at 25° C. and a thermister tip having external dimensions of 0.15×0.15×1.00 mm. The Teflon tube 7 used was an ethylenetetrafluoroethylene copolymer and had an inner diameter of 0.26 mm and an outer diameter of 0.56 mm. Used as a lead wire 9 of the thermister 8 was a copper wire having a diameter of 0.1 mm coated with a polyurethane resin.

The thermister 8 was mounted by bringing it into contact with the redox membrane electrode 10 and depositing the hydrogen ion carrier membrane 5 on the thermister 8 and electrode 10. The hydrogen ion carrier membrane 5 was deposited by maintaining the contact between the redox membrane electrode 10 and thermister 8 and repeatedly dipping the entirety in a hydrogen ion carrier composition, given below, and allowing the same to dry. The dipping and drying steps were repeated 15 times to uniformly coat the entirety of the electrode 10 and thermister 8 with the hydrogen ion carrier membrane 5 to a membrane thickness of about 0.8 mm. The electrode thus coated with the hydrogen ion carrier membrane 5 had a tip portion 11 whose outer diameter was 3.0 mm and a shaft portion 12 whose outer diameter was 2.0 mm. Though sensors were fabricated up to a maximum shaft length 13 of 30 mm, sensors having a shaft length of 25 mm were employed in the experiments described below.

| (Hydrogen Ion Carrier Composition) | |
|---|---|
| tridodecyl amine | 2 mg/ml |
| tetrakis(p-chlorophenyl) potassium borate | 1.2 mg/ml |
| polyvinyl chloride (PVC, $p_n$ = 1050) | 65.6 mg/ml |
| diocytl sebacate (DOS) | 131.2 mg/ml |
| solvent: tetrahydrofuran (THF) | |

EXPERIMENT 3

Figure 4:
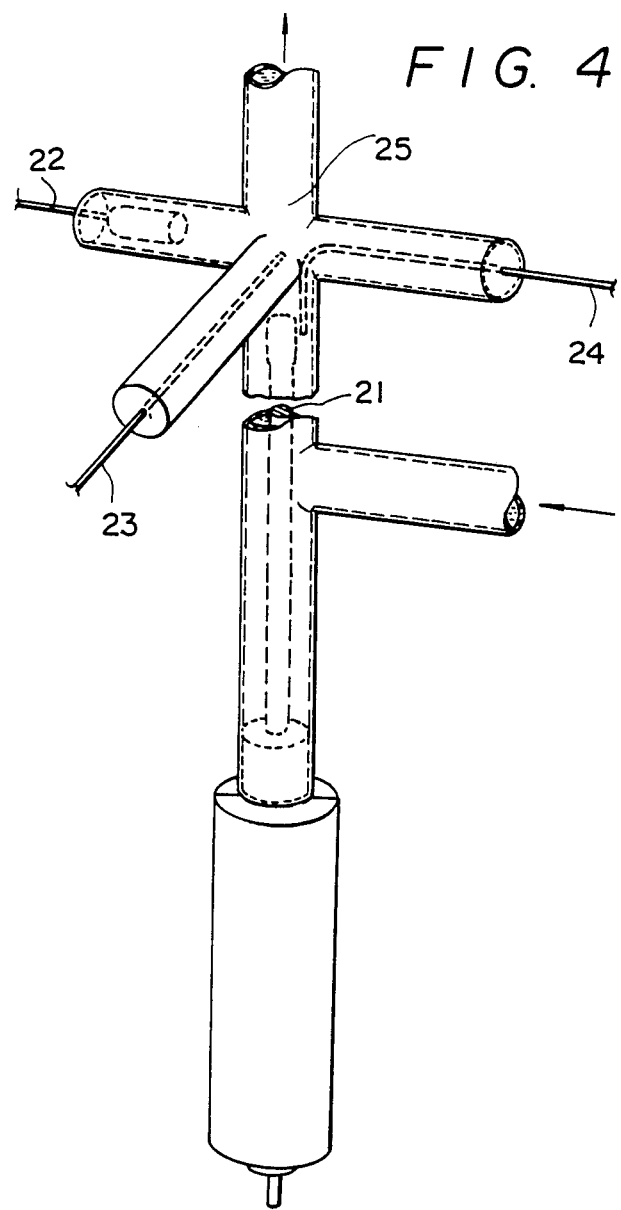
FIG. 4 is a schematic view useful in describing a flow cell used in a performance test of a PH sensor according to the present invention.

A three-pole cell shown in FIG. 4 was set up and the response of the PH sensor with respect to a temperature change was tested. The PH sensor used was that fabricated in Example 5.

(1) Cell

The thermister-equipped PH sensor fabricated in Example 5 was covered by a heat-shrinkable tube 16, and this was then bonded to a two-stage tube 14 of polycarbonate resin by means of a polyurethane adhesive 15. The resulting electrode was employed as a working electrode 21. A platinum mesh was used as a counter electrode 22, and an Ag/AgCl electrode was used as a reference electrode 23. The Ag/AgCl electrode was isolated from the liquid specimen by a porous membrane (ceramic), and a saturated NaCl solution containing an agar-agar gel was employed as the electrolyte. Also arranged in the cell near the tip of the PH sensor was a thermister 24, identical with that used in the PH sensor, coated with an insulating film.

The liquid specimen 25 used was a phosphoric acid buffer solution having a PH of 7.44 at 37° C. The arrangement was such that the liquid specimen could be supplied in a flow, when required. Further, the cell employed PVC tubing having an outer diameter of 8 mm. Following fabrication, the PH sensor employed was immersed for about six hours in a PH 7.44 buffer solution the same as that mentioned above.

(2) Response Experiment

A response experiment was performed by measuring the time needed for electromotive force to attain a steady value when the temperature of the liquid specimen was lowered from 39.36° C. to 19.59° C. and raised from 19.59° C. to 39.36° C. The results are shown in Table 4. It should be noted that the time constant of the thermister used was 50 msec, and that a transient phenomenon on the order of seconds was caused by a transient response of the PH sensor of the invention or by dissipation of heat through this PH sensor.

TABLE 4

|  | Temperature Change | 95% Response | 99.9% Response |
| --- | --- | --- | --- |
| Potential Response of PH Sensor | 39.36→15.59° C. | 10 sec. | 52 sec. |
|  | 39.36←15.59° C. | 35 sec. | 82 sec. |
| Temperature Response Actually Measured by Thermister in Electrode | 39.36→15.59° C. | 8.6 sec. | 12.9 sec. |
|  | 39.36←15.59° C. | 5.8 sec. | 11.8 sec. |

Note: The PH sensor was immersed in the liquid specimen over a length of 25 mm.

EXPERIMENT 4

In FIG. 4, the immersion length of the PH sensor 21 in the liquid specimen was varied from 5 to 30 mm to investigate the relationship between the immersion length and a temperature difference $\Delta T$, namely the difference between the temperature actually measured by the thermister in the electrode and the temperature actually measured by the thermister 24 in the liquid specimen. It should be noted that steady values of temperature were measured. The results are shown in FIG. 5.

Figure 5:
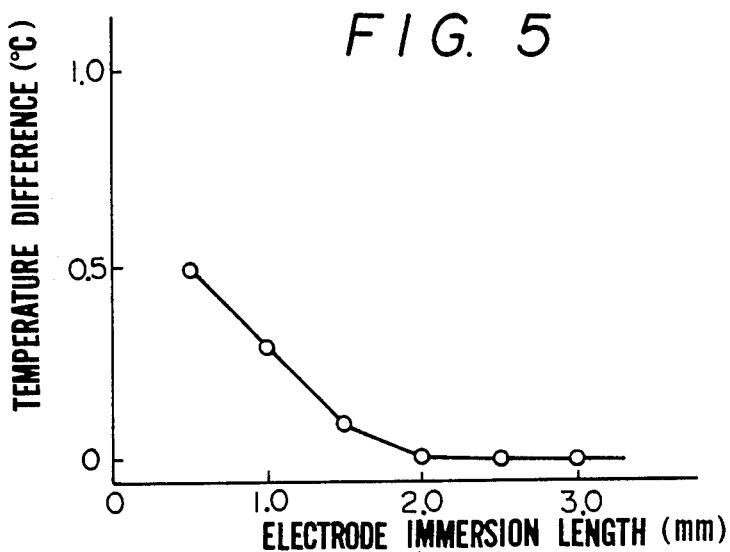
FIG. 5 is a graph in which electrode immersion length is plotted against a difference between temperature measured by a thermister inside an electrode and temperature measured by a thermister in a liquid specimen.

FIG. 5 shows that $\Delta T$ becomes approximately zero when the immersion length exceeds 20 mm. It may also be understood from FIG. 5 that if the immersion length is less than 20 mm, the temperature within the electrode does not become the same as that of the liquid specimen owing to conduction of heat through the shaft of the PH sensor. Accordingly, it will be understood that if the electrode is immersed in the liquid specimen to a length of 20 mm or more, in the PH sensor fabricated in Example 5, the temperature internally of the electrode and the temperature of the liquid specimen will coincide in about ten seconds (see Experiment 3), and a transient phenomenon after ten seconds is caused by the sensor itself. It will also be understood that, in accordance with the sensor of the present invention, PH can be measured accurately at the temperature of the liquid specimen approximately one minute after any temperature change that might occur in the specimen.

The PH sensor of the present embodiment does not possess an internal liquid chamber and has a membrane which exhibits excellent selectivity. This makes it possible to use the sensor continuously over an extended period of time. Since the sensor has a internal thermister, as mentioned above, temperature differences between a liquid specimen and the interior of the electrode can be monitored. For example, this makes it possible to determine whether a transient response accompanying a change in the temperature of the liquid specimen is due to an unsteady temperature or a delay in the sensor response. This enables a more accurate measurement of ion concentration without the influence of temperature changes.

EXAMPLE 6

The PH sensor shown in FIG. 1 was fabricated in accordance with the following steps and will be described in conjunction with FIG. 1:

(1) Fabrication of redox membrane electrode

The lead wire 3 (copper wire, 20E-CN-15W, manufactured by Totoku K.K.) was connected by means of the electrically conductive adhesive 2 (C-850-6, manufactured by Amicon) to the bottom surface 1a of BPG 1 having a diameter of 1.0 mm and a length of 3.5 mm. The periphery of the lead wire 3 and BPG 1 were insulated with the Teflon 6 (Polyflon TC-7408GY, manufactured by Daikin Kogyo). Next, the redox membrane 4 was deposited directly on the BPG 1 by performing electrolytical oxidation under the following conditions using a three-electrode cell in which the BPG electrode served as the working electrode, a carbon plate (thickness 2 mm×30 mm×30 mm) as the counter electrode, and an Ag/AgCl electrode as the reference electrode:

(Electrolyte Composition

An acetonitrile solution consisting of 0.5M 2,6-xylenol and 0.2 M $NaClO_4$ was employed as the electrolytic solution.

(Electrolytic Oxidation Polymerization Conditions

The electrolyzing voltage was swept three times (sweep rate: 50 mV/sec) from 0V (vs. the Ag/AgCl electrode) to 1.5V, followed by carrying out constant-potential electrolysis for b 10 min at 1.5V. Polymerization temparature was carried out at $-20°$ C.

(2) Fabrication of PH sensor

A hydrogen ion carrier membrane having the composition given below was deposited to a thickness of 1 mm on the surface of the redox membrane electrode fabricated in (1) above. The membrane was deposited by dipping the redox membrane electrode in a tetrahydrofuran mixture solution having the composition given below, followed by drying. This procedure was repeated 15 times to obtain the PH sensors shown in Table 5.

TABLE 5

| (Hydrogen Ion Carrier Composition) | |
| --- | --- |
| dioctyl sebacate (DOS) | 200 parts by weight |
| polyvinyl chloride (PVC, $p_n = 1050$) | 100 parts by weight |
| tridodecyl amine (TDDA) | (see Table 5) |
| tetrakis(p-chlorophenyl) potassium borate (KTpClPB) | (see Table 5) |

| PH Sensor | TDDA (parts by weight) | KTpClPB (parts by weight) | Membrane Resistance (37° C.) (MΩ) | Slope of* Nernst Plot (mV/PH) |
| --- | --- | --- | --- | --- |
| Example 1 | 9 | 1.8 | 0.941 | −60.5 |
| Example 2 | 12 | 1.8 | 0.586 | −62.9 |
| Example 3 | 18 | 1.8 | 0.396 | −62.1 |
| Example 4 | 24 | 1.8 | 0.593 | −63.2 |

*Nernst plot is shown electromotive force of PH sensor vs. PH.

COMPARATIVE EXAMPLE

PH sensors serving as products for comparison shown in Table 6 were fabricated as in Example 6 except for the fact that the loads of TDDA and KTpClPB in the hydrogen ion carrier composition were changed.

TABLE 6

| Ph Sensor | TDDA (parts by weight) | KTpClPB (parts by weight) | Membrane Resistance (37° C.) (M) | Slope of Nernst Plot (mv/PH) |
| --- | --- | --- | --- | --- |
| Product 1 | 0 | 1.8 | 3.27 | No Response |
| Product 2 | 3 | 0 | 16.8 | −61.1 |
| Product 3 | 3 | 1.8 | 2.19 | −59.3 |
| Product 4 | 3 | 3.6 | 0.773 | −13.2 |

*Nernst plot is shown electromotive force of PH sensor vs. PH.

Experiment 5

Using the PH sensor fabricated in Example 6, the response thereof with respect to a step change in the temperature of a liquid specimen 45 (a phosphoric acid buffer solution having a PH of 7.44) was investigated as follows:

(Experimental Method)

Figure 6:
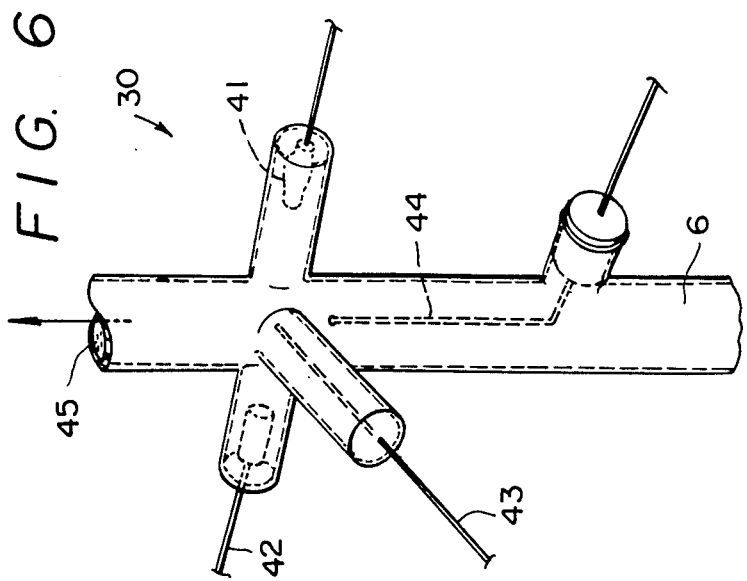
FIG. 6 is a schematic view useful in describing a flow cell.
Figure 7:
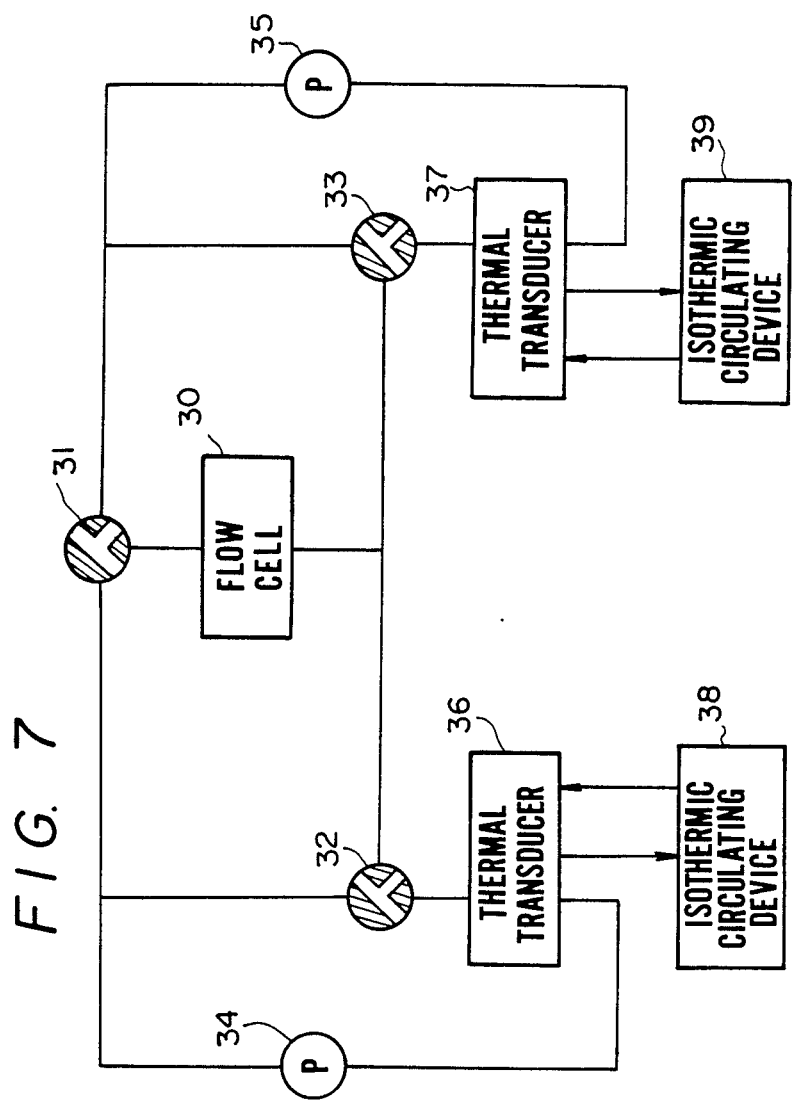
FIG. 7 is a flow diagram showing a circulating system for producing temperature steps in a solution temperature.

A flow cell 30 made of pliable PVC tubing having a diameter of 8 mm, as shown in FIG. 6, was used as an experimental cell. A PH sensor 41 fabricated in Example 6 was inserted into the cell to a depth of 2.5 mm and the electromotive force between the sensor and a reference electrode 42 was measured as a differential output voltage with respect to a common electrode 43. The temperature of the solution was changed in steps by constructing the circulating system shown in FIG. 7 using thermal transducers 36, 37 and isothermic circulating devices 38, 39, setting up a flow velocity of 1 l/min by roller pumps 34, 35, instantaneously switching the flow, in which the solution temperature is held constant at 36.68° C. and 18.08° C., by three-way cocks 31, 32, 33, and measuring the solution temperature in the measurement section by a thermister 44.

(Results)

Figure 8:
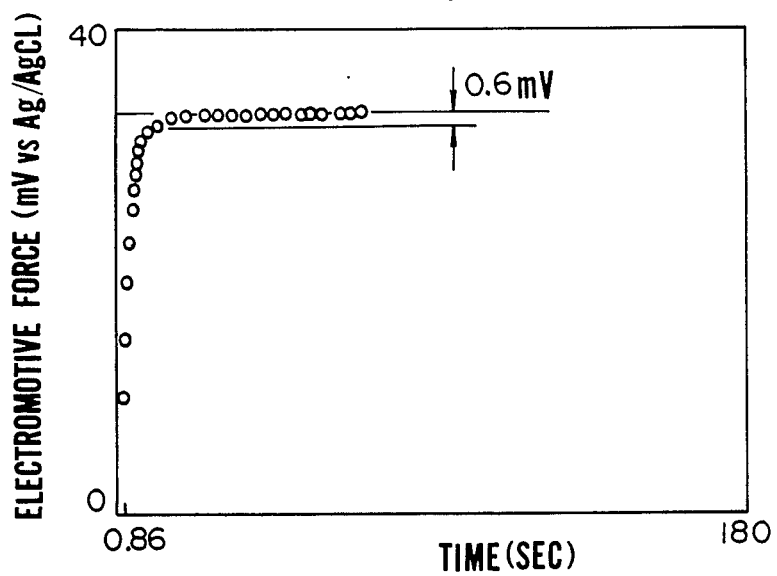
Figure 9:
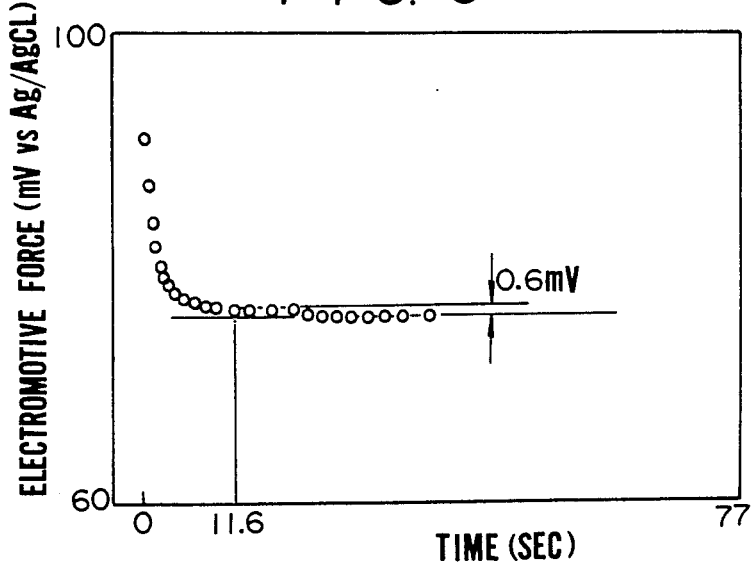

FIGS. 8 and 9 illustrate response curves with respect to step-like changes in temperature for the sensor fabricated in Example 6.

As shown in FIGS. 8 and 9, the time required to attain a range of ±0.6 mV of a steady value was 8.6 sec when the temperature was elevated from 18.08° to 38.08° C. (FIG. 8) and 11.6 sec when the temperature was lowered from 38.08° to 18.08° C. (FIG. 9). It should be noted that the time needed to attain ±0.6 mV is taken as the indicator of performance because ±0.6 mV corresponds to about ±0.01 in terms of PH value and is a range which allows sufficiently precise measurements to be taken.

Experiment 6

The responses of the sensors of Examples 1, 3, 4 and of Product 3 with respect to a step change in temperature were investigated as in Experiment 5. The results are shown in FIG. 10, which also includes the results of Experiment 5.

Figure 10:
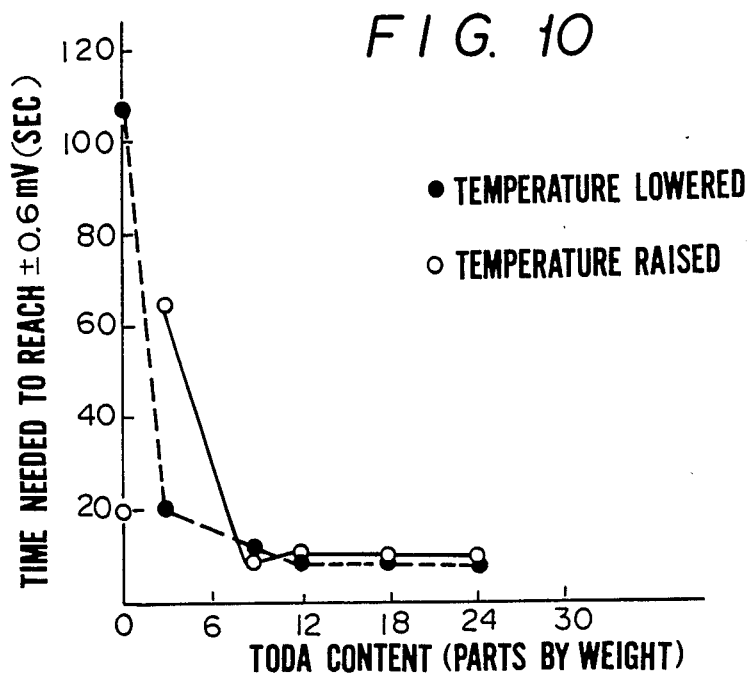

It will be understood from FIG. 10 that the speed of response (the time needed to attain ±0.6 mV) was a quick ten seconds for 9 parts by weight of TDDA with respect to 100 parts by weight of polyvinyl chloride.

Experiment 7

The responses of the Products 2, 3, 4 with respect to a step change in temperature were investigated as in Experiment 5. The results are shown in FIG. 11.

As shown in FIG. 11, a quick response was obtained in a KTpClPB range of 0–3.6 parts by weight for 3 parts by weight of TDDA with respect to 100 parts by weight of polyvinyl chloride. Though a quicker response was observed when the KTpClPB content was increased, the PH dependence of the Nernst plot decreased, as shown in Table 6. This is undesirable. The preferred range is 0–3.0 parts by weight.

EXAMPLE 7

The PH sensors shown in Table 7 were fabricated by depositing hydrogen ion carrier membranes having the compositions shown in Table 7 to a thickness of 0.8–1.0 mm on the redox membrane electrode fabricated in Example 6(1). The method used was the same as in Example 6(2). Next, the response of the PH sensors to a step change in temperature was tested as in Experiment 5. The results are shown in FIG. 12.

TABLE 7

| PH Sensor | DOS* | PVC* | TDDA* | KTpClPB* | Membrane Resistance (MΩ) | Slope of Nernst Plot (mV/PH)** |
|---|---|---|---|---|---|---|
| Product 5 | 34.2 | 100 | 4.03 | 0.81 | — | No Response |
| Example 5 | 85.2 | 100 | 5.56 | 1.11 | 0.759 | −59.9 |
| Example 6 | 128.3 | 100 | 6.85 | 1.37 | 0.492 | −59.0 |
| Example 7 | 200 | 100 | 9 | 1.8 | 0.941 | −60.5 |
| Example 8 | 327.3 | 100 | 12.82 | 2.56 | 0.442 | −60.9 |
| Example 9 | 662.5 | 100 | 22.88 | 4.58 | 0.584 | −57.5 |

*parts by weight
**Nernst plot is shown electromotive force of PH sensor vs. PH.

By virtue of the above construction, the PH sensor of the present embodiment is capable of attaining an equilibrium value within ten seconds with regard to a sudden temperature change of 20° C. or more. This makes possible accurate measurement of ionic concentration even in a flow system where the temperature of the liquid specimen undergoes a rapid change.

What we claim is:

1. An ion sensor comprising:
   an electrically conductive substrate;
   an electrically polymerized redox layer having a redox function covering a surface of said electrically conductive substrate; and
   an ion-selective layer exhibiting ion selectivity covering a surface of said redox layer wherein said ion selective layer contains the following ingredients (a) - (d):

| | | |
|---|---|---|
| (a) | a polyvinyl chloride | 100 parts by weight |
| (b) | ion carrier material | 6–30 parts by weight |
| (c) | electrolytic salt | 0–3.6 parts by weight |
| (d) | plasticizers | 40–665 parts by weight. |

2. The ion sensor according to claim 1, wherein said electrically conductive substrate is selected from a group consisting of an electrically conductive carbon material, a metal, and a composite obtained by coating the surface of said metal with a semiconductor.

3. An ion sensor according to claim 2, wherein said metal comprises gold, platinum, copper, silver, palladium, nickel or iron, said conductive carbon material comprises basal plane pyrolytic graphite or glassy carbon and said semiconductor comprises indium oxide or tin oxide.

4. The ion sensor according to claim 1, wherein said redox layer is selected from the group of materials which undergo a quinone-hydroquinone type redox reaction.

5. The ion sensor according to claim 1, wherein said redox layer is selected from the group of materials which undergo an amine-quinoid type redox reaction.

6. The ion sensor according to claim 1, wherein said redox layer is selected from the group of electrically conductive materials consisting of poly (pyrrole) and poly (thionylene).

7. The ion sensor according to claim 1, wherein said redox layer has a thickness of from 0.01 μm to 1.0 mm.

8. The ion sensor according to claim 1, wherein said ion-sensitive layer has a thickness of from 1 μm to 10 mm.

9. The ion sensor according to claim 1, wherein said ion-sensitive layer comprises a polymeric membrane containing an ion carrier material, which is a compound expressed by the formula

where $R^1$, $R^2$, $R^3$ represent the same or different alkyl groups, among which at least two alkyl groups have a carbon number of 8-18, and is selective to hydrogen ion.

10. The ion sensor according to claim 1, wherein said ion selective layer has an electrode resistance of no more than 50MΩ at 10° C.

11. The ion sensor according to claim 1, wherein said ion-sensitive layer comprises an organic polymeric membrane containing an ion carrier material, which is a compound expressed by the formula

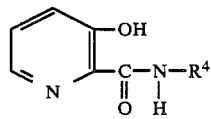

where $R^4$ represents an alkyl group having a carbon number of 8-18, and is selective to hydrogen ion.

12. The ion sensor according to claim 1, wherein said ion-sensitive layer comprises a polymeric membrane containing an ion carrier material, which is selected from the group consisting of crown ether compounds including valinonycin, nonactin and monactin, and is selective to potassium ion.

13. An ion sensor according to claim 12 wherein said crown ether compounds comprise dicyclohexyl-18-crown-6, naphtho-15-crown-5, bis (15-crown-5).

14. The ion sensor according to claim 1, wherein said ion-sensitive layer comprises a polymeric membrane containing an ion carrier material, which is selected from the group consisting of aromatic amides or diamides, aliphatic amides or diamides, and crown compounds, and is selective to sodium ion.

15. The ion sensor according to claim 1, wherein said ion-sensitive layer comprises a polymeric membrane containing an ion carrier material, which is selected from the group of the quaternary ammonium salts expressed by the formula

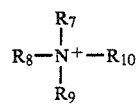

where $R_7$, $R_8$, $R_9$ represent the same or different alkyl groups which have a carbon number of 8-10, and $R_{10}$ represents hydrogen or an alkyl group having a carbon number of 1-8, and is selective to chlorine ion.

16. The ion sensor according to claim 1, wherein said ion-sensitive layer comprises a polymeric membrane containing an ion carrier material, which is expressed by the formula

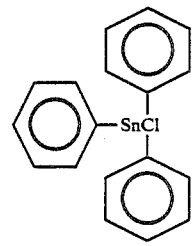

and is selective to chlorine ion.

17. The ion sensor according to claim 1, wherein said ion-sensitive layer comprises a polymeric membrane containing an ion carrier material, which is selected from the group consisting of calcium bis(di-(n-octylphenyl) phosphate , (-)-(R,R)-N,N'-bis((11-ethoxy carbonyl) undecyl)-N,N',4,5-tetramethyl-3,6-dioxaoctanediamide and calcium bis(di(n-decyl) phosphate), and is selective to calcium ion.

18. The ion sensor according to claim 1, wherein said ion-sensitive layer comprises a polymeric membrane containing an ion carrier material, which is selected from the group of quaternary ammonium salts expressed by the formula

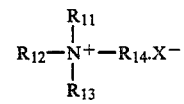

where $R_{11}$, $R_{12}$, $R_{13}$ represent the same or different alkyl groups having a carbon number of 8-18, $R_{14}$ represents hydrogen atom or an alkyl group having a carbon number of 1-4, and $X^-$ represents $Cl^-$, $Br^-$ or $OH^-$, and is selective to hydrogencarbonate ion.

19. The ion sensor according to claim 1, wherein said ion-sensitive layer comprises a polymeric membrane containing an ion carrier material, which is selected from the group of tertiary amine compounds expressed by the formulae

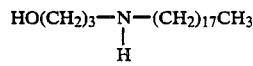

and

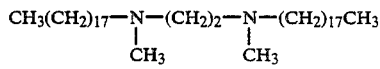

and is selective to hydrogencarbonate ion.

20. The ion sensor according to claim 1, wherein said ion-sensitive layer comprises a polymeric membrane containing an ion carrier material, which is selected from the group of nonacting consisting of monactin and tetranactine, and is selective to ammonium ion.

21. The ion sensor according to claim 1, wherein said ion-sensitive layer comprises an organic polymeric membrane containing an ion carrier material selective to magnesium ion.

22. An ion sensor according to claim 21, wherein the ion carrier material is N, N'-diheptyl-N,N'-dimethyl-1,4-butane diamine.

23. The ion sensor according to claim 1, wherein said ion-sensitive layer comprises a polymeric membrane containing an ion carrier material, which is a tertiary amine compound selective to hydrogencarbonate ion.

24. An ion sensor comprising:
an electrically conductive substrate having a tip;
a redox layer having a redox function covering a surface of said electrically conductive substrate; and
a thermister coated with an insulating membrane and imbedded adjacent the tip of said electrically conductive substrate so as to contact said redox layer; and
an ion-selective layer covering a surface of said redox layer and of said insulating membrane which covers said thermister.

25. The ion sensor according to claim 24, wherein said electrically conductive substrate is selected from a group which consists of an electrically conductive carbon material, a metal, and a composite obtained by coating the surface of said metal with a semiconductor.

26. An ion sensor according to claim 25, wherein said metal comprises gold, platinum, copper, silver, palladium, nickel or iron, said conductive carbon material comprises basal plane pyrolytic graphite or glassy carbon and said semiconductor comprises indium oxide or tin oxide.

27. The ion sensor according to claim 24, wherein said redox layer is selected from the group of materials which undergo a quinone-hydroquinone type redox reaction.

28. The ion sensor according to claim 24, wherein said redox layer is selected from the group of materials which undergo an amine-quinoid type redox reaction.

29. The ion sensor according to claim 24, wherein said redox layer is selected from the group of electrically conductive materials consisting of poly (pyrrole) and poly (thionylene).

30. The ion sensor according to claim 24, wherein said redox layer has a thickness of from 0.01 $\mu$m to 1.0 mm.

31. The ion sensor according to claim 24, wherein said ion-sensitive layer has a thickness of from 1 $\mu$m to 10 mm.

32. The ion sensor according to claim 24, wherein said ion-sensitive layer comprises a polymeric membrane containing an ion carrier material, which is a compound expressed by the formula

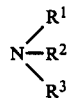

where $R^1$, $R^2$, $R^3$ represent the same or different alkyl groups, among which at least two alkyl groups have a carbon number of 8-18, and is selective to hydrogen ion.

33. The ion sensor according to claim 24, wherein said ion selective layer has an electrode resistance of no more than 50 M$\Omega$ at 10° C.

34. The ion sensor according to claim 24, wherein said ion selective layer contains the following ingredients (A)

| - (D): | |
|---|---|
| (A) polyvinyl chloride: | 100 parts by weight |
| (B) ion carrier material: | 6-30 parts by weight |
| (C) electrolytic salt | 0-3.6 parts by weight |
| (D) plasticizer | 40-665 parts by weight |

35. The ion sensor according to claim 24, wherein said ion-sensitive layer comprises a polymeric membrane containing an ion carrier material, which is a compound expressed by the formula

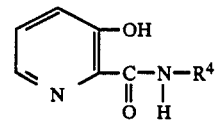

where $R^4$ represents an alkyl group having a carbon number of 8-18, and is selective to hydrogen ion.

36. The ion sensor according to claim 24, wherein said ion-sensitive layer comprises a polymeric membrane containing an ion carrier material, which is selected from the group consisting of crown ether compounds including valinomycin, nonactin and monactin, and is selective to potassium ion.

37. An ion sensor according to claim 36 wherein said crown ether compounds comprise dicyclohexyl-18-crown-6,naphtho-15-crown-5,bis (15-crown-5).

38. The ion sensor according to claim 24, wherein said ion-sensitive layer comprises a polymeric membrane containing an ion carrier material, which is selected from the group consisting of aromatic amides or diamides, aliphatic amides or diamides, and crown compounds, and is selective to sodium ion.

39. The ion sensor according to claim 24, wherein said ion-sensitive layer comprises a polymeric membrane containing an ion carrier material, which is selected from the group of the quaternary ammonium salts expressed by the formula

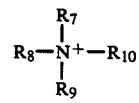

where $R_7$, $R_8$, $R_9$ represent the same or different alkyl groups which have a carbon number of 8-10, and $R_{10}$ represents hydrogen or an alkyl group having a carbon number of 1-8, and is selective to chlorine ion.

40. The ion sensor according to claim 24, wherein said ion-sensitive layer comprises a polymeric membrane containing an ion carrier material, which is expressed by the formula

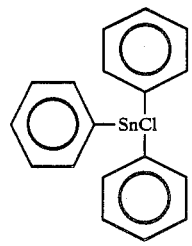

and is selective to chlorine ion.

41. The ion sensor according to claim 24, wherein said ion-sensitive layer comprises a polymeric membrane containing an ion carrier material, which is selected from the group consisting of calcium bis(di-(n-octylphenyl) phosphate), (-)-(R,R)-N,N'-bis(11-ethoxy carbonyl) undecyl)-N,N',4,5-tetramethyl-3,6-dioxaoctane-diamide and calcium bis(di(n-decyl) phosphate), and is selective to calcium ion.

42. The ion sensor according to claim 24, wherein said ion-sensitive layer comprises a polymeric membrane containing an ion carrier material, which is selected from the group of quaternary ammonium salts expressed by the formula

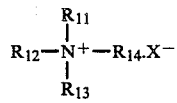

where $R_{11}$, $R_{12}$, $R_{13}$ represent the same or different alkyl groups having a carbon number of 8-18, $R_{14}$ represents hydrogen atom or an alkyl group having a carbon number of 1-4, and $X^-$ represents $Cl^-$, $Br^-$ or $OH^-$, and is selective to hydrogencarbonate ion.

43. The ion sensor according to claim 24, wherein said ion-sensitive layer comprises a polymeric membrane containing an ion carrier material, which is selected from the group of tertiary amine compounds expressed by the formulae

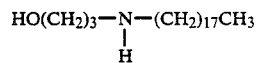

and

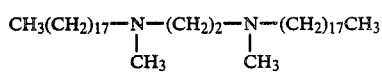

and is selective to hydrogencarbonate ion.

44. The ion sensor according to claim 24, wherein said ion-sensitive layer comprises a polymeric membrane containing an ion carrier material, which is selected from the group of nonactins consisting of monactin and tetranactine, and is selective to ammonium ion.

45. The ion sensor according to claim 24, wherein said ion-sensitive layer comprises a polymeric membrane containing an ion carrier material selective to magnesium ion.

46. The ion sensor according to claim 24, wherein said ion-sensitive layer comprises a polymeric membrane containing an ion carrier material, which is a tertiary amine compound selective to hydrogencarbonate ion.

47. An ion sensor comprising:
an electrically conductive substrate;
a redox layer electrolytically polymerized at about $-20°$ C. having a redox function covering a surface of said electrically conductive substrate; and
an ion-selective layer exhibiting ion selectivity covering a surface of said redox layer.

* * * * *